United States Patent [19]

Johnson et al.

[11] Patent Number: 4,758,669

[45] Date of Patent: Jul. 19, 1988

[54] 4-(NITRONE ARYL) DIHYDROPYRIDINES

[75] Inventors: Carl R. Johnson; John D. Taylor, both of Detroit; Kenneth V. Honn, Grosse Pointe Woods, all of Mich.; Soan Cheng, East Palo Alto, Calif.

[73] Assignee: Radiation Oncology Center Research and Development Corporation, Detroit, Mich.

[21] Appl. No.: 859,694

[22] Filed: May 5, 1986

[51] Int. Cl.⁴ .................. C07D 211/90; C07D 401/12; C07D 405/12; C07D 409/12

[52] U.S. Cl. ..................................... 546/263; 546/281; 546/283; 546/284; 546/321

[58] Field of Search ................ 546/321, 263, 281, 283, 546/284; 514/356

[56] References Cited

U.S. PATENT DOCUMENTS 3,799,934  3/1974  Meyer et al. ......................... 546/321
4,406,906  9/1983  Meyer et al. ......................... 514/356
4,462,992  7/1984  Agrawal et al. ...................... 548/338

OTHER PUBLICATIONS

Hyatt, JOC 49, 5102–5105 (1984).
Hyatt, JOC 49, 5105–5108 (1984).
Kato et al., in Chem Pharm. Bull., 30, 1315–1321 (1982).
Iwanami, J. et al., Chem Pharm. Bull., 27, pp. 1426–1440 (1979).
Advances in Cancer Res., Chapter VII, Academic Press Inc. (1978).
Honn et al., Clinical & Experimental Metastisis, vol. 2, 61–72 (1984).

Primary Examiner—Mary C. Lee
Assistant Examiner—Dale A. Bjorkman
Attorney, Agent, or Firm—Ian C. McLeod

[57] ABSTRACT

Novel nitrone substituted 4-aryl dihydropyridines of the formula:

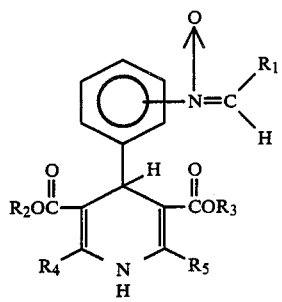

are described along with a process for their preparation. The compounds exhibit calcium channel blocker and antimetastatic acitivity.

14 Claims, 5 Drawing Sheets

FIG. 1a: ANTITHROMBOGENIC EFFECTS OF NOVEL COMPOUNDS (1000 μM)
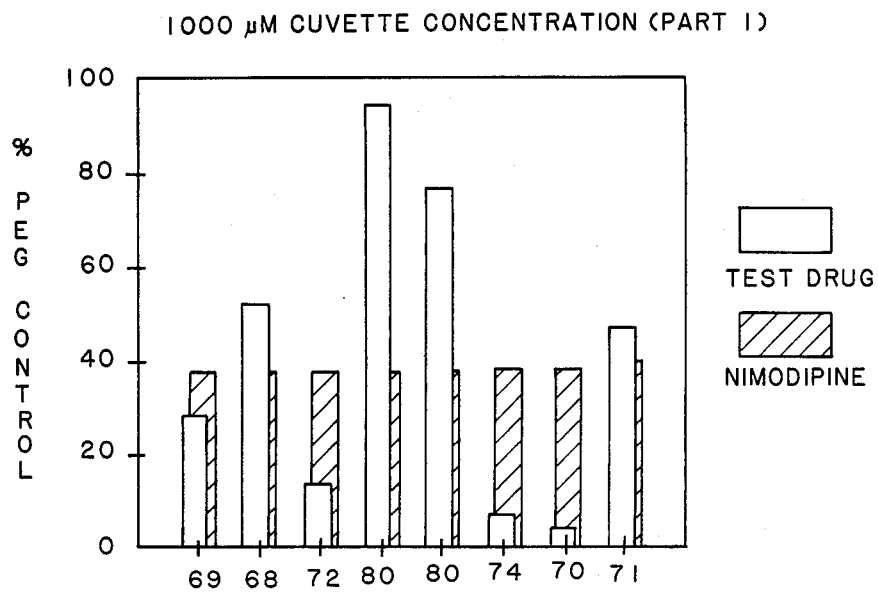
FIG. 1b
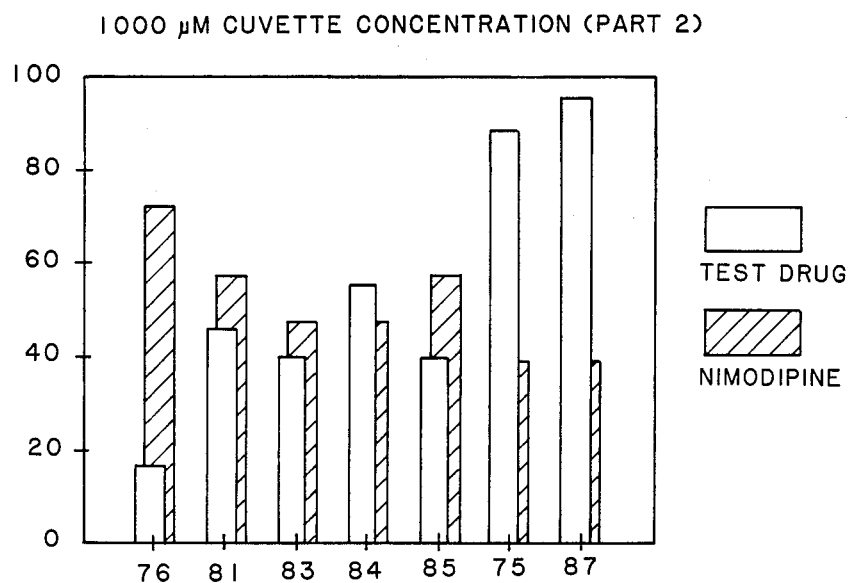

FIG. 2a: ANTITHROMBOGENIC EFFECTS OF NOVEL COMPOUNDS (250 μM)
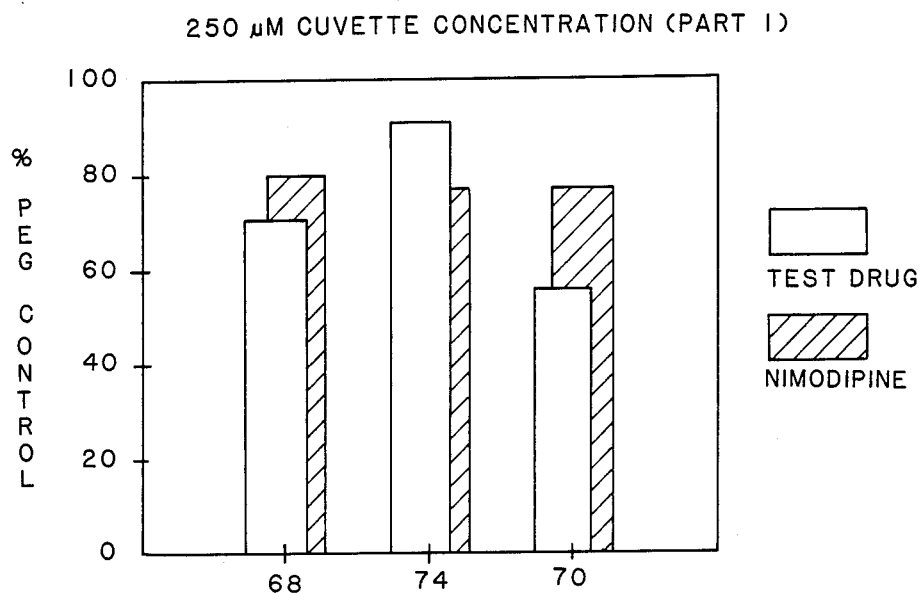
FIG. 2b
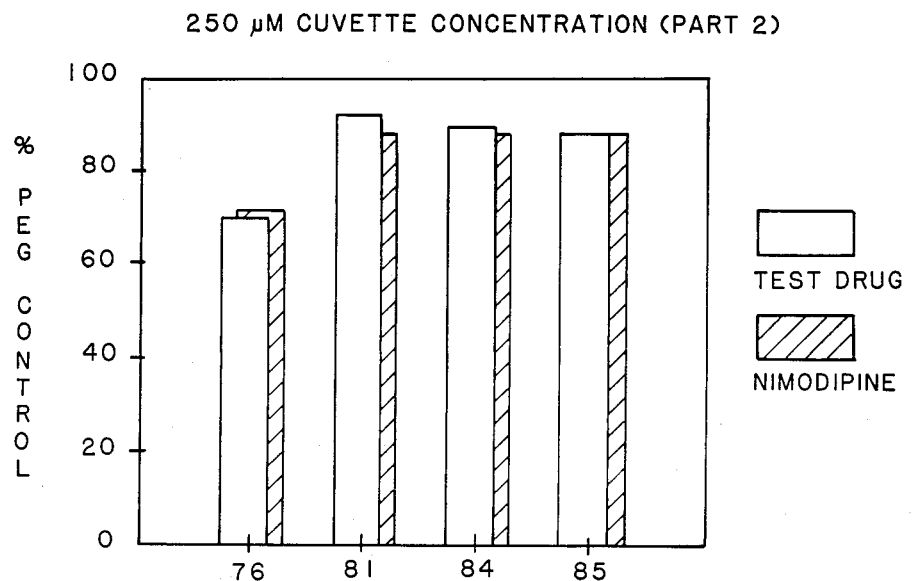

EFFECT OF 207 ON TUMOR COLONY FORMATION

C = CONTROL
ip-1 = i.p. INJECTION OF 207 3 & 6 HR PRIOR TO t.c. INJECTION
ip-2 = i.p. INJECTION OF 207 24, 6 & 1 HR PRIOR TO t.c. INJECTION
po = ORAL INJECTION OF 207 4, 2, & 1/2 HR PRIOR TO t.c. INJECTION AND 1/2 HR AFTER t.c. INJECTION

4-(NITRONE ARYL) DIHYDROPYRIDINES

BACKGROUND OF THE INVENTION (1) Field of the Invention

The present invention relates to novel 4-(nitrone aryl)dihydropyridines which exhibit antimetastatic and antithrombic properties and to a process for their preparation. In particular the present invention relates to preferred compounds where the aryl group is a nitrophenyl group.

(2) Prior Art

The prior art describes 4-aryl dihydropyridines which are useful as cardiovascular agents. U.S. Pat. No. 4,406,906 to Meyer et al describes the use of 1,4-dihydro-2,6-dimethyl-4-(3'nitrophenyl)-pyridine-3-(betamethoxyethyl ester)-5-(isopropyl ester) as an agent for cerebral vascular disorders, also known as nimodipene. U.S. Pat. No. 3,799,934 to Meyer et al also describes a large number of these compounds. The compounds are generally classed as calcium channel blockers because of the mode of action as described in detail in U.S. patent application Ser. No. 480,704, filed Mar. 31, 1985 filed by some of the inventors herein. Application Ser. No. 480,704 also describes the use of the 4-aryl dihydropyridines as antimetastatic agents.

OBJECTS

It is therefore an object of the present invention to provide novel 4-(nitrone aryl)dihydropyridines which exhibit calcium channel blocker and antimetastatic activity. The present invention also relates to novel processes for the preparation of these compounds. These and other objects will become increasingly apparent by reference to the following description and the drawings.

IN THE DRAWINGS

FIGS. 1a and 1b are graphs showing the antithrombic effects of the compounds of the present invention in vitro at a 1000 microMolar concentration versus nimodipene.

FIGS. 2a and 2b are graphs showing the antithrombic effects of the compounds in vitro at a 250 microMolar concentration versus nimodipene.

Figure 3:
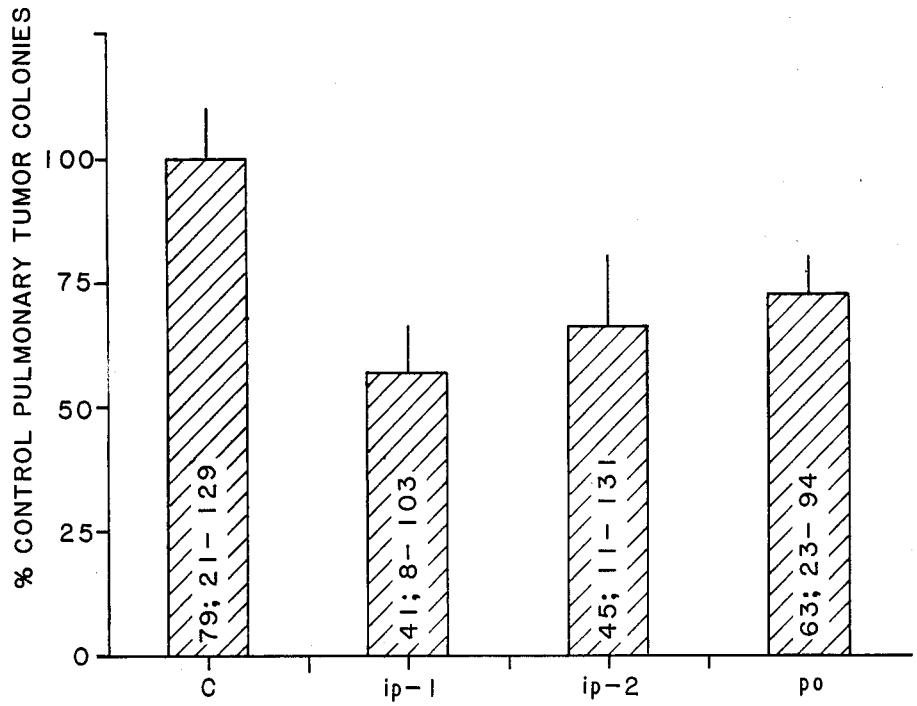
FIG. 3 is a graph showing the antimetastatic effects of one of the compounds (70) of the present invention which was most active in the in vitro testing using mouse tail vein injection of tumor cells.

The present invention relates to a 4-(nitrone aryl)-dihydropyridine compound of the formula:

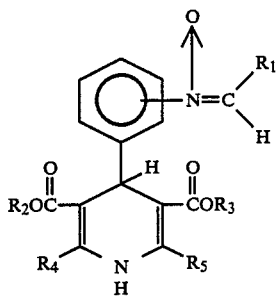

(1)

wherein $R_1$ is selected from substituted and unsubstituted aryl groups and carbon attached O, S and N heterocyclic groups containing 4 to 5 carbon atoms and wherein $R_2$ and $R_3$ are selected from lower alkyl and alkoxy (lower alkyl) and wherein $R_4$ and $R_5$ are lower alkyl.

The present invention also relates to a process for producing a 4-(nitrone aryl)dihydropyridine of the formula:

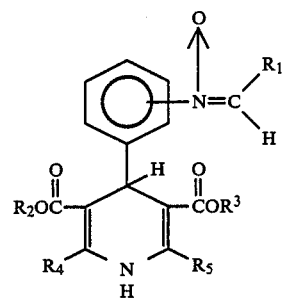

(1)

wherein $R_1$ is selected from substituted and unsubstituted aryl groups and carbon attached O, S and N heterocyclic groups containing 4 to 5 carbon atoms and wherein $R_2$ and $R_3$ are selected from lower alkyl and alkoxy (lower alkyl) and wherein $R_4$ and $R_5$ are lower alkyl which comprises:

(a) treating a 4-nitrophenyl dihydropyridine of the formula:

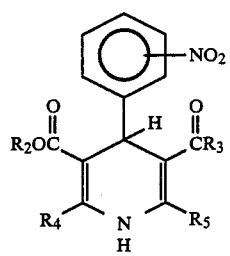

(1)

with a reducing agent in a solvent to form a hydroxylamine of the formula:

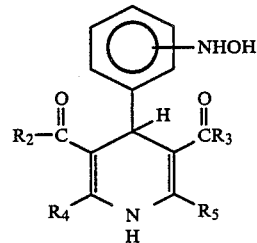

(b) treating the hydroxylamine with a substituted or unsubstituted aldehyde of the formula $R_1CHO$ in a solvent to form the 4-(nitrone aryl)dihydropyridine.

The present invention further relates to a process for producing a 4-(nitrone aryl)dihydropyridine of the formula:

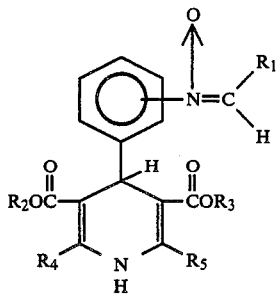
(1)

wherein $R_1$ is selected from substituted and unsubstituted aryl groups and carbon attached O, S and N heterocyclic groups containing 4 to 5 carbon atoms and wherein $R_2$ and $R_3$ are selected from lower alkyl and alkoxy (lower alkyl) and wherein $R_4$ and $R_5$ are lower alkyl which comprises:

(a) treating in a reaction mixture a nitrone aldehyde of the formula

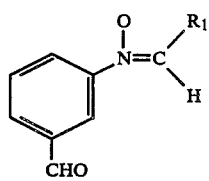

with a first compound of the formula

and a second compound of the formula

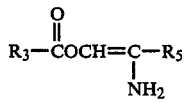

in a polar organic solvent containing a Lewis base, such as ammonium acetate; and (b) separating the 4-(nitrone aryl)dihydropyridine from the reaction mixture.

The primary object of the synthesis was unique examples of (1) involving variations of $R_1$ in the formula

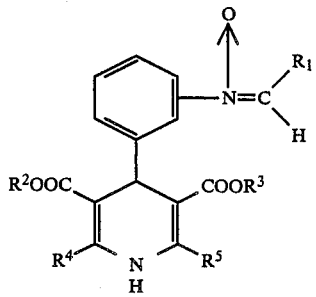
1

It is believed that calcium channel blocking activity is enhanced by the presence of bulky groups which cause the 4-nitrone aryl group to prefer an orientation perpendicular to the plane of the dihydropyridine ring. The electronegative nitro group in the ortho or meta positions has been found to result in excellent biological activity (e.g., nifedipine, nimodipine). The inventors reasoned that enhanced biological activity might be observed by maintaining the electronegativity characteristic of the nitro group while adding additional steric bulk. The nitrone variations of 4-aryl dihydropyridine were particularly attractive target molecules. The nitrone group is related electronically to the nitro group and has the additional steric bulk afforded by the replacement of the oxygen by the arylmethylene,

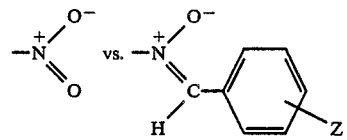

where Z is hydrogen or one or more substituents in the aryl group which are generally electron withdrawing.

The starting material, nimodipine (50), chosen for the synthesis of nitrone target was prepared by the modified Hantzsch reaction. Condensation of 3-nitro-benzaldehyde, 2-methoxyethyl acetoacetate (51) and 1-methylethyl 3-aminocrotonate (52) in 2-propanol gave nimodipine (50) in 58% yield (eq. 27) as shown in Scheme I.

SCHEME I (eq. 27)

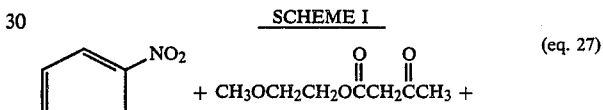

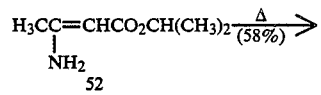

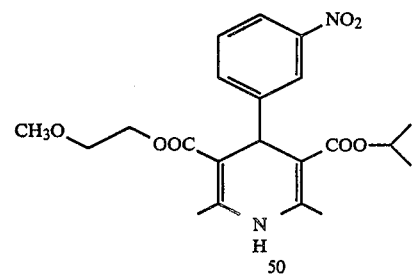

The ester, 2-methoxyethyl acetoacetate (51), was prepared by the reaction of 2-methoxyethanol with 2,2,6-trimethyl-4H-1,3-dioxin-4-one (53) (eq. 28). (Hyatt, J. A. J. Org. Chem. 1984, 49, 5102. Hyatt, J. A.; Feldman, P. L.; Clemens, R. J. Ibid. 1984, 49, 5105. Kato, T.; Sato, M.; Kanuma, N. Chem. Pharm. Bull. 1982, 30, 1315). The enamine, 1-methylethyl 3-aminocrotonate (52) was prepared by the reaction of ammonia with 1-methylethyl acetoacetate (54) (eq. 29) (Iwanami, J. et al. Chem. Pharm. Bull. 27, 1426 (1979)) which was obtained by the reaction of 2-propanol with 53 (eq. 30) as shown in Schemes IIa, IIb and IIc.

SCHEME IIa

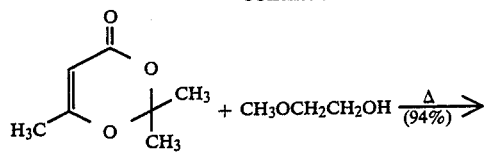

SCHEME IIc

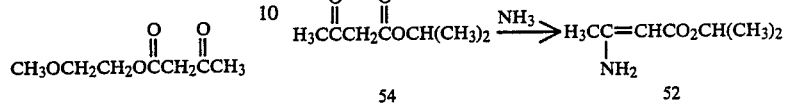

Nitrone targets were prepared by the condensation of aldehydes with the common intermediate hydroxylamine (55) which was obtained from the mild reduction (Zn/NH4Cl) of the nitro group of nimodipine (50) (Scheme III) hereinafter. A compilation of the results of this reaction sequence is provided in Table I. The reaction conditions are very mild and most reactions were performed at room temperature. The yields are fair to good for the substituted benzaldehydes 56–62 and heteroaromatic carboxaldehydes 63–65. The only exception is the π excessive heteroaromatic carboxaldehyde, 1-methyl-2-pyrrolecarboxaldehyde (66).

SCHEME IIb

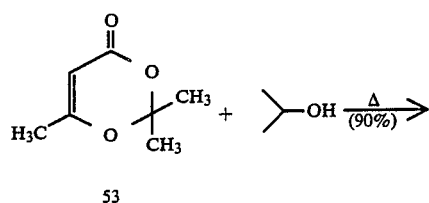

TABLE I

Preparation of Compound 67–77.

| Aldehyde | Product | % Yield[a,b] |
|---|---|---|
| 56 (benzaldehyde, PhCHO) | 67 | 86 |
| 57 (3-nitrobenzaldehyde) | 68 | 77 |

TABLE I-continued

Preparation of Compound 67-77.

| Aldehyde | Product | % Yield[a,b] |
|---|---|---|
| 2-chlorobenzaldehyde (61) | Compound 72 | 80 |
| 4-chlorobenzaldehyde (62) | Compound 73 | 75 |
| pyridine-2-carbaldehyde (63) | Compound 74 | 77 |

TABLE I-continued

Preparation of Compound 67-77.

| Aldehyde | Product | % Yield[a,b] |
|---|---|---|
| 4-nitrobenzaldehyde (58) | Compound 69 | 71 |
| 2-nitrobenzaldehyde (59) | Compound 70 | 75 |
| 3-(trifluoromethyl)benzaldehyde (60) | Compound 71 | 75 |

TABLE I-continued
Preparation of Compound 67-77.
| Aldehyde | Product | % Yield[a,b] |
|---|---|---|
| 64 (thiophene-2-CHO) | 75 | 86 |
| 65 (5-nitrofuran-2-CHO) | 76 | 81 |
| 66 (N-methylpyrrole-2-CHO) | 77 | 40 |
[a]Isolated yields.
[b]Based on two step reactions (hydroxylamine 55 was prepared and condensed with aldehydes without further purification).
Scheme III
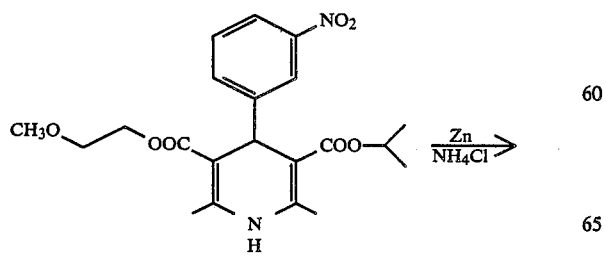
-continued
Scheme III

Scheme III -continued

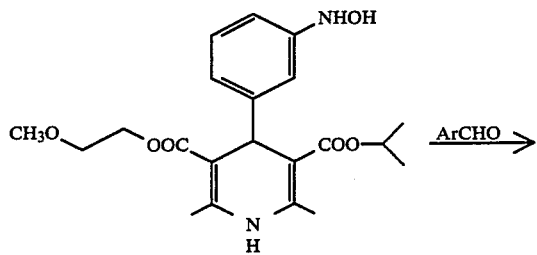

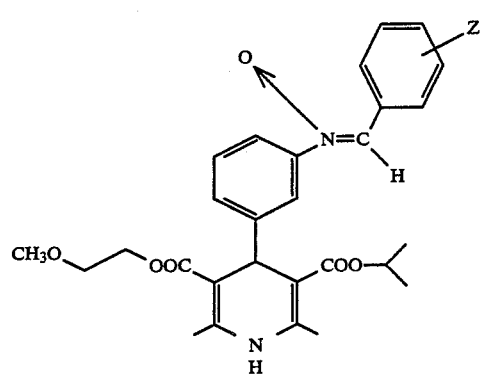

The other starting material chosen for the synthesis of nitrone targets was methyl 1-methylethyl 1,4-dihydro-2,6-dimethyl-4-(3-nitrophenyl)-3,5-pyridinedicarboxylate (81). It has been observed that (−)-(81) has a potency greater than nifedipine or nimodipine.[73]

Compound 81 was prepared in 62% yield by a modified Hantzsch reaction, condensation of 3-nitrobenzaldehyde, methyl acetoacetate and 1-methylethyl 3-aminocrotonate in 2-propanol (eq. 31) Scheme IV.

Scheme IV

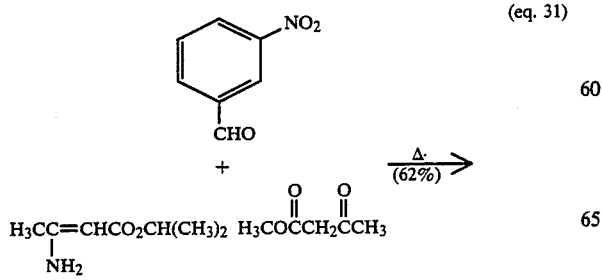

Scheme IV -continued

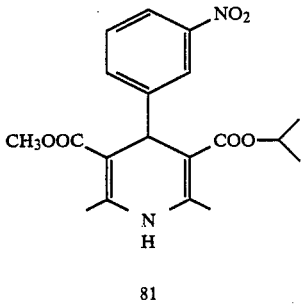

The common intermediate hydroxylamine 82 was obtained from the mild reduction (Zn/NH$_4$Cl) of the nitro group of 81. Various nitrone targets were prepared by the condensation of aldehydes with 81 (Scheme V). A compilation of the results of this reaction sequence is provided in Table II.

Scheme V

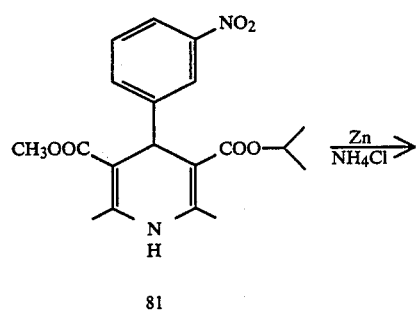

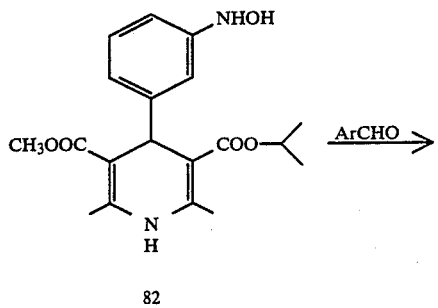

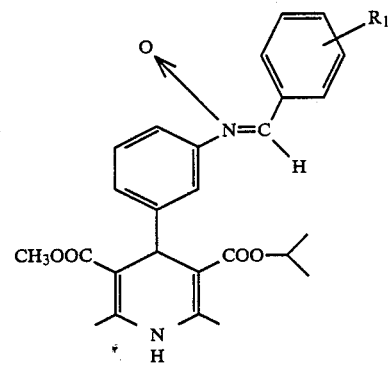

TABLE II

Preparation of Compound 83–87.

| Aldehyde | Product | % Yield[a,b] |
|---|---|---|
| 3-NO₂-C₆H₄-CHO (57) | Compound 83 | 72 |
| 2-NO₂-C₆H₄-CHO (59) | Compound 84 | 72 |
| 3-CF₃-C₆H₄-CHO (60) | Compound 85 | 78 |

TABLE II-continued
Preparation of Compound 83–87.

| Aldehyde | Product | % Yield[a,b] |
|---|---|---|
| <br>63 | 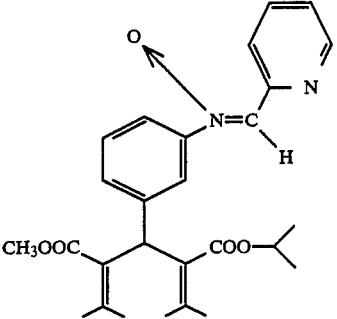<br>86 | 72 |
| <br>64 | 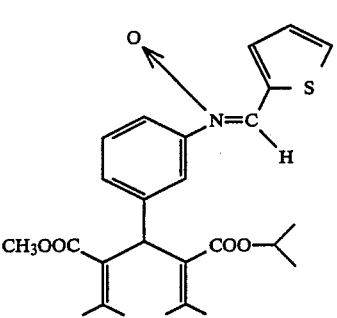<br>87 | 71 |

[a]Isolated yields.
[b]Based on two step reactions (hydroxylamine 82 was prepared and condensed with aldehydes without further purification).

An alternate synthesis for this class of compounds without using the nimodipine (50) and 81 as the precursors has also been developed.

The sequence of reactions utilized in the synthesis of 89 is outlined in Scheme VI.

Mild reduction (Zn/NH₄Cl) of the nitro group of 3-nitrobenzyl alcohol (90) gave the hydroxylamine 91. Condensation of 3-nitrobenzaldehyde with hydroxylamine 91 gave the nitrone 92 in 70% yield. Manganese dioxide oxidation of the benzylic hydroxyl group of 92 gave 89 in 69% yield.

SCHEME VI

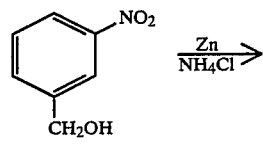
90

-continued
SCHEME VI

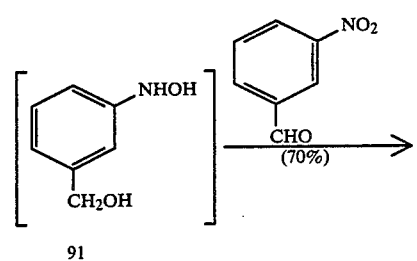
91

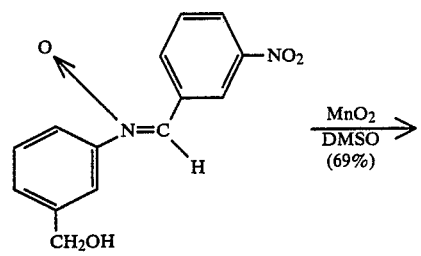
92

-continued
SCHEME VI

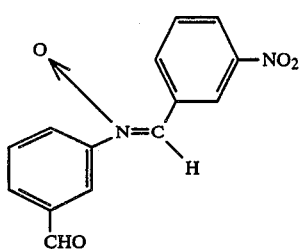

89

A compilation of the results of the condensation of hydroxylamine 91 with other aldehydes is provided in Table III.

Condensation of 89, 2-methoxyethyl acetoacetate (51) and 1-methylethyl 3-aminocrotonate (52) in the presence of ammonium acetate gave the desired product 68 in 26% yield (eq. 33), Scheme VII.

TABLE III

Preparation of Compound 92-96.

| Aldehyde | Product | % Yield[a,b] |
|---|---|---|
| 57 (3-NO₂-benzaldehyde) | 92 | 70 |
| 58 (4-NO₂-benzaldehyde) | 93 | 81 |
| 59 (2-NO₂-benzaldehyde) | 94 | 64 |
| 65 (5-nitrofuran-2-carbaldehyde) | 96 | 71 |

TABLE III-continued

Preparation of Compound 92-96.

| Aldehyde | Product | % Yield[a,b] |
|---|---|---|
| 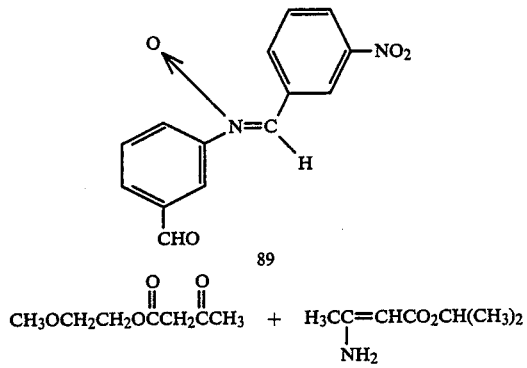 | | 65 |

[a] Isolated Yields
[b] Based on two step reactions (hydroxylamine 91 was prepared and condensed with aldehydes without further purification).

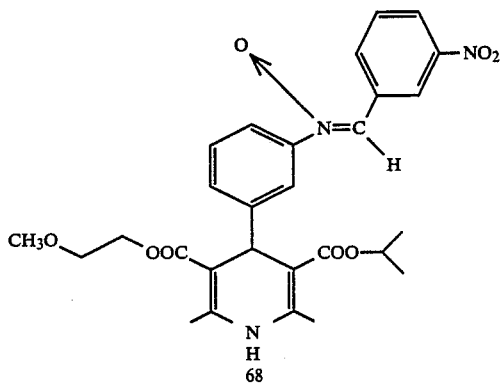

(eq. 33)

EXPERIMENTAL SECTION

General Procedures

All air-sensitive reactions were conducted in flame- or oven-dried apparatus under a positive pressure of argon. Air-sensitive liquids were transferred by syringe or double-ended needle and introduced to the reaction vessel through rubber septum caps. All reaction mixtures were stirred magnetically unless otherwise indicated.

Materials

Unless otherwise noted, commercial grade reagents and reagent grade solvents were used without further purification. The following solvents were dried as indicated:

Benzene, toluene, dimethylsulfoxide (DMSO): distilled from calcium hydride and stored over 4 Å molecular sieves.

Dichloromethane: distilled under argon from phosphorous pentoxide.

Acetone: stirred over 4 Å molecular sieves.

Zinc powder (purified) was purchased from J. T. Baker Chemical Co.

2-Pyridinecarboxaldehyde was purchased from Aldrich and was distilled before use.

Chromatography

Analytical thin layer chromatography (TLC) was performed on silica gel plates (0.25 mm, EM Reagents). The chromatograms were visualized by one or more of the following techniques: (a) ultraviolet illumination (UV); (b) exposure to iodine vapors ($I_2$); (c) spray of 5% solution of phosphomolybdic acid in isopropanol followed by heating on a hot plate (PMA).

Analytical High Performance Liquid Chromtography (HPLC) was performed on a Varian Associates Model 5000 liquid chromatography equipped with a DuPont Zorbax ™ Sil (5-6 microm) steel column (4.6 mm×25 cm) and a UV detector.

Flash chromatography was performed using silica gel 60 (230-400 mesh, EM Reagents).

Reagent grade solvents were used for flash chromatography without purification. All solvents for analytical HPLC were of commercially available HPLC grade.

Physical Data

Melting points (mp) were determined using a Thomas Hoover melting point apparatus and are uncorrected.

Infrared (IR) spectra were recorded on a Perkin-Elmer 267 or 283-B spectrophotometer and are reported in wave numbers ($cm^{-1}$). The spectra were calibrated with the 1601 $cm^{-1}$ absorption of polystyrene film.

Proton nuclear magnetic resonance ($^1$H-NMR) spectra were measured at 60 MHz on a Varian T60 or %60-A spectrometer and a 300.15 MHz on a General Electric QE-300 spectrometer. Chemical shifts were reported in parts per million downfield from tetramethylsilane (%).

Carbon-13 ($^{13}$C-NMR) spectra were measured at 75.48 MHz on a General Electric QE-300 spectrometer. Chemical shifts were reported in parts per million downfield from tetramethylsilane ($\delta$).

Mass spectra were recorded on AEI-MS-902 spectrometer at 24 or 70 eV.

Microanalyses were performed by Midwest Microlabs, Indianapolis, Ind.

2-Methoxyethyl Acetoacetate (51)

A solution of 2,2,6-trimethyl-4H-1,3-dioxin-4-one(53)[70] (74 g, 0.5 mol) and 2-methoxyethanol (38 g, 0.5 mol) was heated at 135° C. for 22 h. The acetone formed during the reaction was removed with a rotary evaporator. The residue was distilled to provide 75 g (0.468 mol, 94%) of 51 as a clear, colorless liquid: bp 120° C. (20 mm).

1-Methylethyl Acetoacetate (54)

A solution of 2,2,6-trimethyl-4H-1,3-dioxin-4-one (53)[70] (74 g, 0.5 mol) and 2-propanol (30 g, 0.5 mol) was heated at 135° C. for 20 h. The acetone formed during the reaction was removed with a rotary evaporator. The residue was distilled to provide 65 g (0.451 mol, 90%) of 54 as a clear, colorless liquid: bp 185°-187° C.

1-Methylethyl 3-Aminocrotonate (52) was prepared according the the procedure of Iwanami.[32]

2-Methoxyethyl 1-Methylethyl 1,4-Dihydro-2,6-dimethyl-4-(3-nitrophenyl)-3,5-pyridinedicarboxylate (50)

A solution of 2-methoxyethyl acetoacetate (51) (32 g, 0.2 mol), 1-methylethyl 3-aminocrotonate (52) (28.8 g, 0.2 mol) and 3-nitrobenzaldehyde (30.6 g, 0.2 mol) in 2-propanol (280 mL) was refluxed for 9 h. The mixture was diluted with dichloromethane (1000 mL) and dried (MgSO$_4$), and the solvent was removed with a rotary evaporator. The crude produce was recrystallized from ethyl acetate-petroleum ether to afford 48 g (0.115 mol, 58%) of 50 as a yellow crystalline solid: mp 122°-123° C. (lit.[81] mp 125° C.); IR (CH$_2$Cl$_2$) 3440, 2975, 1692, 1620, 1530, 1460, 1345, 1210, 1095 $cm^{-1}$; $^1$H NMR (CDCl$_3$) $\delta$ 1.08 (d, J=6.2 Hz, 3H), 1.25 (d, J=6.2 Hz, 3H), 2.33 (s, 6H), 3.33 (s, 3H), 3.55 (t, J=4.8 Hz, 2H), 4.12-4.20 (m, 2H), 4.93 (septet, J=6.2 Hz, 1H), 5.09 (s, 1H), 6.31 (s, 1H), 7.34-8.13 (m, 4H); $^{13}$C NMR (CDCl$_3$) $\delta$ 19.38, 19.53, 21.85, 22.17, 40.14, 58.90, 63.05, 67.43, 70.58, 102.93, 103.75, 121.36, 123.33, 128.70, 134.81, 144.84, 145.62, 148.16, 150.20, 166.75, 167.26.

2-Methoxyethyl 1-Methylethyl 1,4-Dihydro-2,6-dimethyl-4-(3-hydroxylaminophenyl)-3,5-pyridinedicarboxylate (55)

To a solution of 1 (0.84 g, 2 mmol) and NH$_4$Cl (0.26 g, 4.85 mmol) in 86% aqueous ethanol (22 mL) was added zinc powder (0.52 g, 7.95 mmol). The resulting mixture was stirred vigorously at room temperature for 50 min. The mixture was filtered and the solvent was poured into dichloromethane (100 mL). The solution was washed with water (40 mL) and dried (MgSO$_4$), and the solvent was removed with a rotary evaporator to obtain 0.80 g of 2 as a yellow oil which was condensed with aldehydes without further purification. IR (CH$_2$Cl$_2$) 3575, 3440, 1700, 1625, 1475, 1300, 1218, 1105 $cm^{-1}$; $^1$H NMR (CDCl$_3$) $\delta$ 1.12 (d, J=6.2 Hz, 3H), 1.23 (d, J=6.2 Hz, 3H), 2.26 (s, 6H), 3.35 (s, 3H), 3.58 (t, J=4.8 Hz, 2H), 4.12-4.26 (m, 2H), 4.95 (septet, 1H), 4.99 (s, 1H), 6.21 (br s, 1H), 6.43 (br s, 1H), 6.75-7.28 (m, 4H); $^{13}$C NMR (CDCl$_3$) $\delta$ 19.37, 19.52, 21.92, 22.20, 39.76, 58.88, 62.78, 67.20, 70.74, 103.44, 104.33, 112.73, 114.54, 122.07, 128.40, 144.03, 144.98, 148.64, 149.82, 167.48, 167.92.

General Procedures for the Preparation of Compound 67-76

To a solution of hydroxyamine 55 (0.80 g, 2 mmol) in anhydrous ethyl alcohol (20 mL) was added aldehyde (2 mmol) and Na$_2$SO$_4$ (0.40 g). The resulting mixture was stirred at room temperature until the TLC analysis indicated no starting material (30 min-6 h). The mixture was diluted with dichloromethane (100 mL) and dried (MgSO$_4$), and the solvent was removed with a rotary evaporator to afford the crude product.

2-Methoxyethyl 1-Methylethyl 1,4-Dihydro-2,6-dimethyl-4-{3-[(Z)-N-oxo-N-(phenylmethylene)-$\lambda^5$-azanyl]phenyl}-3,5-pyridinedicarboxylate (67)

The reaction of hydroxylamine 55 (0.80 g, 2 mmol) with benzaldehyde (56)(0.21 g, 2 mmol) afforded, after workup, a yellow oil. The crude product was purified by flash chromatography with 1:1 ethyl acetate/hexane as the eluant to obtain 0.85 g (1.72 mmol, 86%) of 67 as a light yellow gum; IR (CH$_2$Cl$_2$) 3440, 2975, 1692, 1620, 1552, 1470, 1298, 1212, 1100 $cm^{-1}$; $^1$H NMR (CDCl$_3$, 60 MHz) $\delta$ 1.16 (t, J=6 Hz, 6H), 2.26 (s, 6H), 3.30 (s, 3H), 3.50 (t, J=5 Hz, 2H), 4.16 (t, J=5 Hz, 2H), 4.70-5.06 (m, 2H), 6.86 (bs, 1H), 7.30-8.46 (m, 10H). Anal. Calcd for C$_{28}$H$_{32}$N$_2$O$_6$: C, 68.29; H, 6.50. Found: C, 68.16; H, 6.31.

2-Methoxyethyl 1-Methylethyl 1,4-Dihydro-2,6-dimethyl-4-{3-[(Z)-N-(3-nitrophenylmethylene)-N-oxo-λ⁵-azanyl]phenyl}-3,5-pyridinedicarboxylate (68)

The reaction of hydroxylamine 55 (0.80 g, 2 mmol) with 3-nitrobenzaldehyde (57) (0.302 g, 2 mmol) afforded, after workup, a yellow solid. The crude product was recrystallized from dichloromethane-petroleum ether to afford 0.82 g (1.53 mmol, 77%) of 68 as a light yellow crystalline solid: mp 175°–178° C.; IR (CH$_2$Cl$_2$) 3440, 2980, 1695, 1620, 1550, 1532, 1470, 1350, 1295, 1210, 1100, 905, 810 cm$^{-1}$; $^1$H NMR (CDCl$_3$) δ 1.11 (d, J=6.2 Hz, 3H), 1.23 (d, J=6.2 Hz, 3H), 2.29 (s, 6H), 3.32 (s, 3H), 3.58 (t, J=4.8 Hz, 2H), 4.20 (m, 2H), 4.94 (septet, J=6.2 Hz, 1H), 5.09 (s, 1H), 6.46 (s, 1H), 7.32–9.28 (m, 9H); $^{13}$C NMR (CDCl$_3$) δ 19.38, 19.48, 21.97, 22.20, 40.09, 58.82, 62.85, 67.28, 70.72, 102.95, 103.74, 119.45, 121.46, 123.39, 124.88, 128.68, 129.76, 130.68, 132.25, 132.37, 134.13, 144.77, 145.57, 148.44, 148.61, 149.94, 166.96, 167.43; mass spectrum, m/e (relative intensity) 537 (M$^+$, 0.1), 296 (100), 254 (66.6), 196 (67.2), 150 (15.8), 59 (20.6), 43 (21.1), 28 (73.7). Anal. Calcd for C$_{28}$H$_{31}$N$_3$O$_8$: C, 62.57; H, 5.77. Found: C, 62.74; H, 5.60.

2-Methoxyethyl 1-Methylethyl 1,4-Dihydro-2,6-dimethyl-4-{3-[(Z)-N-(4-nitrophenylmethylene)-N-oxo-λ⁵-azanyl]phenyl}-3,5-pyridinedicarboxylate (69)

The reaction of hydroxylamine 55 (0.80 g, 2 mmol) with 4-nitrobenzaldehyde (58) (0.30 g, 2 mmol) afforded, after workup, a yellow oil. The crude product was purified by flash chromatography with 1:1 ethyl acetate/hexane as the eluant to obtain 0.76 g (1.42 mmol, 71%) of 69 as a yellow oil. The oil crystallized from ethyl acetate-pentane to yield red crystalline solid: mp 148°–150° C.; IR (CH$_2$Cl$_2$) 3435, 29980, 1695, 1620, 1598, 1545, 1520, 1470, 1342, 1215, 1102, 858; $^1$H NMR (CDCl$_3$) δ 1.08 (d, J=6.2 Hz, 3H), 1.19 (d, J=6.2 Hz, 3H), 2.25 (s, 6H), 3.28 (s, 3H), 3.55 (t, J=4.8 Hz, 2H), 4.16 (m, 2H), 4.92 (septet, J=6.2 Hz, 1H), 5.06 (s, 1H), 6.66 (s, 1H), 7.27–8.51 (m, 9H); $^{13}$C NMR (CDCl$_3$) δ 19.78, 19.88, 22.45, 22.68, 40.60, 59.26, 63.36, 67.79, 71.19, 103.34, 104.16, 119.97, 122.05, 124.43, 129.24, 129.84, 131.23, 132.97, 137.03, 145.36, 146.17, 148.45, 149.23, 150.50, 167.46, 167.94. Anal. Calcd for C$_{28}$H$_{31}$N$_3$O$_8$: C, 62.57; H, 5.77. Found: C, 62.76, H, 5.82.

2-Methoxyethyl 1-Methylethyl 1,4-Dihydro-2,6-dimethyl-4-{3-[(Z)-N-(2-nitrophenylmethylene)-N-oxo-λ⁵-azanyl]phenyl}-3,5-pyridinedicarboxylate (70)

The reaction of hydroxylamine 55 (0.80 g, 2 mmol) with 2-nitrobenzaldehyde (59) (0.302 g, 2 mmol) afforded, after workup, a yellow oil. The crude product was purified by flash chromatography with 1:1 ethyl acetate/hexane as the eluant to obtain 0.80 g (1.49 mmol. 75%) of 70 as a yellow oil. The oil crystallized from ether-petroleum ether to yield yellow crystalline solid: mp 114°–116° C.; IR (CH$_2$Cl$_2$) 3440, 2980, 1700, 1625, 1575, 1528, 1470, 1345, 1300, 1215, 1105, 905, 852, 775 cm$^{-1}$; $^1$H NMR (CDCl$_3$) δ 1.10 (d, J=6.2 Hz, 3H), 1.23 (d, J=6.2 Hz, 3H), 2.29 (s, 6H), 3.31 (s, 3H), 3.56 (t, J=4.8 Hz, 2H), 4.19 (m, 2H), 4.93 (septet, J=6.2 Hz, 1H), 5.07 (s, 1H), 6.54 (s, 1H), 7.30–9.25 (m, 9H); $^{13}$C NMR (CDCl$_3$) δ 19.98, 20.02, 22.47, 22.72, 40.34, 51.67, 67.85, 103.69, 104.37, 120.22, 121.84, 125.25, 125.61, 128.97, 129.17, 130.11, 131.01, 131.08, 134.11, 145.29, 145.82, 148.17, 149.75, 150.35, 167.43, 168.46; mass spectrum, m/e (relative intensity) 522 (0.2), 518 (10.8), 386 (13.3), 326 (22.5), 296 (100), 254 (53.4), 196 (44.7), 121 (18.9). Anal. Calcd for C$_{28}$H$_{31}$N$_3$O$_8$: C, 62.57; H, 5.77. Found C, 62.72; H, 5.80.

2-Methoxyethyl 1-Methylethyl 1,4-Dihydro-2,6-dimethyl-4-{3-[(Z-N-oxo-N-(3-trifluoromethylphenylmethylene)-λ⁵-azanyl]phenyl-3,5-pyridinedicarboxylate (71)

The reaction of hydroxylamine 55 (0.80 g, 2 mmol) with α,α,α-trifluoro-m-tolualdehyde (60) (0.348 g, 2 mmol) afforded, after workup, a light yellow solid. The crude product was recrystallized from ethyl acetate/hexane to afford 0.84 g (1.50 mmol, 75%) of 71 as a white crystalline solid: mp 162°–164° C.; IR (CH$_2$Cl$_2$) 3440, 2980, 1698, 1630, 1558, 1475, 1335, 1210, 1105, 905, 810 cm$^{-1}$; $^1$H NMR (CDCl$_3$) δ 1.11 (d, J=6.2 Hz, 3H), 1.23 (d, J=6.2 Hz, 3H), 2.28 (s, 6H), 3.32 (s, 3H), 3.58 (t, J=4.8 Hz, 2H), 4.19 (m, 2H), 4.94 (septet, J=6.2 Hz, 1H), 5.10 (s, 1H), 6.58 (br s, 1H), 7.32–8.77 (m, 9H); $^{13}$C NMR (CDCl$_3$) δ 19.33, 19.45, 21.96, 22.18, 40.06, 58.80, 62.86, 67.26, 70.72, 102.91, 103.71, 119.49, 121.50, 125.54, 127.13, 127.17, 128.60, 129.26, 130.53, 131.53, 131.93, 133.33, 144.82, 145.62, 148.76, 149.90, 166.97, 167.46. Anal. Calcd for C$_{29}$H$_{31}$N$_3$O$_6$F$_3$: C, 62.14; H, 5.53. Found: C, 62.01; H, 5.66.

2-Methoxyethyl 1-Methylethyl 1,4-Dihydro-2,6-dimethyl-4-{3-[(Z)-N-(2-chlorophenylmethylene)-N-oxo-λ⁵-azanyl]phenyl}-3,5-pyridinedicarboxylate (72)

The reaction of hydroxylamine 55 (1.97 g, 5 mmol) with 2-chlorobenzaldehyde (61) (0.70 g, 5 mmol) afforded, after workup, a light yellow oil. The crude product was purified by flash chromatography with 3:5 ethyl acetate/petroleum ether as the eluant to obtain 2.11 g (4.0 mmol, 80%) of 72 as a light yellow gum: IR (CH$_2$Cl$_2$) 3440, 2940, 1690, 1623, 1590, 1550, 1470, 1295, 1202, 1100; $^1$H NMR (CDCl$_3$) δ 1.10 (d, J=6.2 Hz, 3H), 1.22 (d, J=6.2 Hz, 3H), 2.25 (s, 6H), 3.30 (s, 3H), 3.54 (t, J=4.8 Hz, 2H), 4.16 (m, 2H), 4.93 (septet, J=6.2 Hz, 1H), 5.07 (s, 1H), 6.87 (s, 1H), 7.27–9.45 (m, 9H); $^{13}$C NMR (CDCl$_3$) δ 19.69, 19.84, 22.49, 22.72, 40.43, 59.36, 63.40, 67.70, 71.18, 103.32, 104.11, 120.08, 122.09, 127.76, 128.94, 129.04, 129.76, 130.22, 130.94, 131.28, 132.16, 134.30, 145.57, 146.32, 149.83, 150.49, 167.51, 167.99. Anal. Calcd for C$_{28}$H$_{31}$N$_2$O$_6$Cl: C, 63.81; H, 5.88. Found: C, 63.51; H, 6.02.

2-Methoxyethyl 1-Methylethyl 1,4-Dihydro-2,6-dimethyl-4-{3-[(Z)-N-(4-chlorophenylmethylene)-N-oxo-λ⁵-azanyl]phenyl}-3,5-pyridinedicarboxylate (73)

The reaction of hydroxylamine 55 (1.98 g, 5 mmol) with 4-chlorobenzaldehyde (62) (0.70 g, 5 mmol) afforded, after workup, a light yellow oil. The crude product was purified by flash chromatography with 1:1 ethyl acetate/petroleum ether as the eluant to obtain 1.97 g (3.74 mmol, 75%) of 73 as a light yellow gum: IR (CH$_2$Cl$_2$) 3440, 2980, 1700, 1625, 1590, 1550, 1475, 1300, 1215, 1110, 910, 840; $^1$H NMR 1.10 (d, J=6.2 Hz, 3H), 1.22 (d, J=6.2 Hz, 3H), 2.26 (s, 6H), 3.31 (s, 3H), 3.56 (t, J=4.8 Hz, 2H), 4.18 (m, 2H), 4.93 (septet, J=6.2 Hz, 1H), 5.06 (s, 1H), 6.79 (s, 1H) 7.28–8.33 (m, 9H); $^{13}$C NMR (CDCl$_3$) δ 19.77, 19.89, 22.48, 22.71, 40.52, 59.32, 63.35, 67.74, 71.21, 103.29, 104.13, 119.97, 122.02, 129.05, 129.52, 129.81, 130.85, 134.35, 136.94, 145.43, 146.25, 149.25, 150.39, 167.56, 168.01. Anal. Calcd for $C_{28}H_{31}N_2O_6Cl$; C, 63.81; H, 5.88. Found: C, 63.86; H, 5.84.

2-Methoxyethyl 1-Methylethyl 1,4-Dihydro-2,6-dimethyl-4-{3-[(Z)-N-oxo-N-(2-pyridylmethylene)-$\lambda^5$-azanyl]phenyl}-3,5-pyridinedicarboxylate (74)

The reaction of hydroxylamine 55 (4.189, 10 mmol) with 2-pyridinecarboxaldehyde (63) (1.07 g, 10 mmol) afforded, after workup, a yellow oil. The crude product was purified by passing through a short column of silica gel with ethyl acetate as the eluant then recrystallized from ethyl acetate/petroleum ether to obtain 3.80 g (7.7 mmol, 77%) of 74 as a yellow crystalline solid: mp 142°–144° C.; IR ($CH_2Cl_2$) 3440, 2940, 1680, 1622, 1580, 1550, 1470, 1295, 1202, 1100, 820 cm$^{-1}$; $^1$H NMR ($CDCl_3$) δ 1.08 (d, J=6.2 Hz, 3H), 1.22 (d, J=6.2 Hz, 3H), 2.27 (s, 6H), 3.31 (s, 3H), 3.52 (t, J=4.8, 2H), 4.18 (m, 2H) 4.92 (septet, J=6.2 Hz, 1H), 5.08 (s, 1H), 6.62 (s, 1H), 7.27–9.28 (m, 9H), $^{13}$C NMR ($CDCl_3$) δ 19.32, 19.47, 21.93, 22.19, 40.09, 58.86, 62.89, 67.21, 70.67, 102.96, 103.77, 119.42, 121.44, 124.01, 124.62, 128.44, 130.77, 135.63, 136.96, 144.73, 145.50, 148.76, 149.90, 166.91, 167.40; mass spectrum, m/e (relative intensity) 493 (M+, 0.2), 475 (9.2), 432 (6.8), 296 (100), 254 (51.5), 196 (47.7), 182 (31.8). Anal. Calcd for $C_{27}H_{31}N_3O_6$: C, 65.72; H, 6.28. Found: C, 65.58; H, 6.18.

2-Methoxyethyl 1-Methylethyl 1,4-Dihydro-2,6-dimethyl-4-{3-[(Z)-N-oxo-N-(2-thienylmethylene)-$\lambda^5$-azanyl]phenyl}-3,5-pyridinedicarboxylate (75)

The reaction of hydroxylamine 55 (0.80 g, 2 mmol) with 2-thiophenecarboxaldehyde (64) (0.224 g, 2 mmol) afforded, after workup, a light yellow oil. The crude product was purified by flash chromatography with 2:1 ethyl acetate/hexane as the eluant to obtain 0.86 g (1.73 mmol, 86%) of 75 as a yellow gum: IR ($CH_2Cl_2$) 3440, 2940, 1698, 1625, 1560, 1472, 1375, 1298, 1215, 1105, cm$^{-1}$; $^1$H NMR ($CDCl_3$) δ 1.09 (d, J=6.2 Hz, 3H), 1.21 (d, J=6.2 Hz, 3H), 2.28 (s, 6H), 3.32 (s, 3H), 3.56 (t, J=4.8 Hz, 2H), 4.18 (m, 2H), 4.94 (septet, J=6.2 Hz, 1H), 5.09 (s, 1H), 6.99–8.52 (m, 8H); $^{13}$C NMR ($CDCl_3$) δ 19.32, 19.44, 21.99, 22.22, 40.12, 58.85; 62.81, 67.18, 70.74, 102.75, 103.53, 118.83, 120.88, 127.19, 128.53, 129.34, 130.21, 130.29, 131.42, 133.00, 145.12, 145.91, 146.37, 149.97, 167.09, 167.55. Anal. calcd for $C_{26}H_{30}N_2O_6S$: C, 62.65; H, 6.02. Found: C, 62.47; H, 6.10.

2-Methoxyethyl 1-Methylethyl 1,4-Dihydro-2,6-dimethyl-4-{3-[(Z)-N-(5-nitro-2-furyl-methylene)-N-oxo-$\lambda^5$-azanyl]phenyl}-3,5-pyridinedicarboxylate (76)

The reaction of hydroxylamine 55 (0.80 g, 2 mmol) with 5-nitro-2-furaldehyde (65) (0.282 g, 2 mmol) afforded, after workup, a purple oil. The crude product was purified by flash chromatography with 1:1 ethyl acetate/hexane as the eluant to obtain 0.85 g (1.61 mmol, 81%) of 76 as a brown gum; IR ($CH_2Cl_2$) 3440, 1698, 1622, 1528, 1470, 1350, 1215, 1100, 1012, 810 cm$^{-1}$; $^1$H NMR ($CDCl_3$) δ 1.09 (d, J=6.2 Hz, 3H), 1.23 (d, J=6.2 Hz, 3H), 2.33 (s, 6H), 3.35 (s, 3H), 3.55–3.59 (m, 2H), 4.17–4.21 (m, 2H), 4.94 (septet, J=6.2 Hz, 1H), 5.09 (s, 1H), 6.20 (s, 1H), 7.34–8.29 (m, 7H); $^{13}$C NMR ($CDCl_3$) δ 19.49, 19.59, 21.92, 22.18, 40.22, 58.85, 62.91, 67.36, 70.73, 103.11, 103.88, 113.84, 116.76, 118.98, 120.73, 122.43, 128.83, 131.37, 144.54, 145.28, 147.09, 149.47, 150.02, 151.63, 166.83, 167.31. Anal. Calcd for $C_{26}H_{29}N_3O_9$: C, 59.20; H, 5.50. Found: C, 59.47; H, 5.74.

2-Methoxyethyl 1-Methylethyl 1,4-Dihydro-2,6-dimethyl-4-{3-[(Z)-N-(1-Methyl-2-pyrrolylmethylene)-N-oxo-$\lambda^5$-azanyl]phenyl}-3,5-pyridinedicarboxylate (77)

To a solution of hydroxyamine 55 (0.80 g, 2 mmol) in anhydrous ethyl alcohol (5 mL) and toluene (20 mL) was added 1-methyl-2-pyrrolecarboxaldehyde (66) (0.22 g, 2 mmol) and $Na_2SO_4$ (0.30 g). The resulting mixture was heated at reflux for 48 h. The mixture was diluted with dichloromethane (100 mL) and dried ($MgSO_4$), and the solvent was removed with a rotary evaporator. The crude product was purified by flash chromatography with 9:1 ethyl acetate/methanol as the eluant to obtain 0.40 g (0.8 mmol, 40%) of 77 as a light yellow solid: mp 173°–175° C.; IR ($CH_2Cl_2$) 3440, 2940, 1695, 1622, 1575, 1470, 1300, 1212, 1100 cm$^{-1}$; $^1$H NMR ($CDCl_3$) δ 1.10 (d, J=6.2 Hz, 3H), 1.22 (d, J=6.2 Hz, 3H), 2.26 (s, 6H), 3.31 (s, 3H), 3.55 (t, J=4.8 Hz, 2H), 3.71 (s, 3H), 4.11–4.20 (m, 2H), 4.94 (septet, J=6.2 Hz, 1H), 5.08 (s, 1H), 6.30–7.98 (m, 9H); $^{13}$C NMR ($CDCl_3$) δ 19.17, 19.32, 22.01, 22.23, 34.34, 39.98, 58.79, 62.76, 67.04, 70.71, 102.63, 103.45, 109.56, 117.39, 118.95, 121.24, 124.21, 125.59, 128.01, 128.23, 129.62, 145.20, 146.02, 148.30, 149.91, 167.12, 167.60; mass spectrum, m/e (relative intensity) 495 (M+, 3.1), 481 (15.5), 296 (100), 254 (86.1), 184 (90.2), 108 (48.3); high resolution mass spectrum, m/e 495.2362 (calcd. for $C_{27}H_{33}N_3O_6$, 495.2369).

Methyl 1-Methylethyl 1,4-Dihydro-2,6-dimethyl-4-(3-nitrophenyl)-3,5-pyridinedicarboxylate (81)

A solution of methyl acetoacetate (6.73 g, 58 mmol), 1-methylethyl 3-aminocrotonate (52) (8.34 g, 58 mmol) and 3-nitro-benzaldehyde (8.75 g, 58 mmol) in 2-propanol (80 mL0 was refluxed for 9 h. The mixture was diluted with dichloromethane (300 mL0 and dried (MgSo4), and the solvent was removed with a rotary evaporator. The crude product was recrystallized from ethyl acetate/hexane to afford 13.5 g (36 mmol, 62%) of 81 as a yellow crystalline solid: mp 142°–144° C. (lit.[81] mp 147° C.); IR ($CH_2Cl_2$) 3440, 2960, 1695, 1622, 1530, 1470, 1352, 1215, 1100 cm$^{-1}$; $^1$H NMR ($CDCl_3$) δ 1.10 (d, J=6.2 Hz, 3H), 1.25 (d, J=6.2 Hz, 3H), 2.33 (s, 6H), 3.64 (s, 3H), 4.95 (septet, J=6.2 Hz, 1H), 5.07 (s, 1H) 6.30 (s, 1H), 7.34–8.12 (m, 4H); $^{13}$C NMR ($CDCl_3$) δ 19.95, 20.04, 22.35, 22.68, 40.53, 51.67. 67.98, 103.48, 104.19, 121.89, 123.61, 129.23, 135.07, 145.38, 145.91, 148.81, 150.61, 167.29, 168.35.

Methyl 1-Methylethyl 1,4-Dihydro-2,6-dimethyl-4-(3-hydroxylamino-phenyl)-3,5-pyridinedicarboxylate (82)

To a solution of 81 (0.75 g, 2 mmol) and NH4Cl (0.26 g, 4.85 mmol) in 86% aqueous ethanol (22 mL) was added zinc powder (0.52 g, 7.95 mmol). The resulting mixture was stirred vigorously at room temperature for 50 minutes. The mixture was filtered, and the solvent was washed with water (40 mL) and dried ($MgSO_4$), and the solvent was removed with a rotary evaporator to obtain 0.71 g of 82 as a yellow oil which was condensed with aldehydes without further purification.

General Procedures for the Preparation of Compound 83–87

To a solution of hydroxyamine (82) (0.71 g, 2 mmol) in anhydrous ethyl alcohol (20 mL) was added aldehyde (2 mmol) and $Na_2SO_4$ (0.40 g). The resulting mixture was stirred at room temperature until TLC analysis indicated no starting material (30 min–6 h). The mixture was diluted with dichloromethane (100 mL) and dried ($MgSO_4$), and the solvent was removed with a rotary evaporator to afford the crude product. The crude product was purified by recrystallization or by flash chromatography.

Methyl 1-Methylethyl 1,4-Dihydro-2,6-dimethyl-4-{3-[(Z)-N-(3-nitrophenylmethylene)-N-oxo-$\lambda^5$-azanyl]phenyl}-3,5-pyridinedicarboxylate (83)

The reaction of hydroxylamine 82 (0.71 g, 2 mmol) with 3-nitrobenzaldehyde (57) (0.302 g, 2 mmol) afforded, after workup, a light yellow solid. The crude product was recrystallized from ethyl acetate/petroleum ether to obtain 0.71 g (1.44 mmol, 72%) of 83 as a light yellow crystalline solid: mp 149°–151° C.; IR ($CH_2Cl_2$) 3440, 2980, 1700, 1622, 1552, 1535, 1475, 1355, 1300, 1215, 1100, 1018, 810 cm$^{-1}$; $^1$H NMR ($CDCl_3$) δ 1.14 (d, J=6.2 Hz, 3H), 1.25 (d, J=6.2 Hz, 3H), 2.30 (s, 6H), 3.64 (s, 3H), 4.97 (septet, J=6.2 Hz, 1H), 5.08 (s, 1H), 6.37 (s, 1H), 7.32–9.29 (m, 9H); $^{13}$C NMR ($CDCl_3$) δ 19.78, 22.47, 22.70, 40.51, 51.58, 67.81, 103.27, 103.99, 119.82, 121.99, 123.79, 125.43, 129.16, 130.24, 131.05, 132.75, 132.94, 134.75, 145.57, 146.11, 148.91, 149.20, 150.56, 167.59, 168.60. Anal. Calcd for $C_{26}H_{27}N_3O_7$: C, 63.28; H, 5.47. Found: C, 63.49; H, 5.47.

Methyl 1-Methylethyl 1,4-Dihydro-2,6-dimethyl-4-{3-[(Z)-N-(2-nitrophenylmethylene)-N-oxo-$\lambda^5$-azanyl]phenyl}-3,5-pyridinedicarboxylate (84)

The reaction of hydroxylamine 82 (0.71 g, 2 mmol) with 2-nitrobenzaldehyde (59) (0.302 g, 2 mmol) afforded, after workup, a yellow oil. The crude product was purified by flash chromatography with 3:4 ethyl acetate/petroleum ether as the eluant to obtain 0.71 g (1.44 mmol, 72%) of 84 as a yellow oil. The oil crystallized from ether/petroleum ether to yield yellow crystalline solid: mp 130°–132° C.; IR ($CH_2Cl_2$) 3440, 2980, 1700, 1625, 1575, 1528, 1470, 1345, 1300, 1215, 1105, 905, 852, 775 cm$^{-1}$; $^1$H NMR ($CDCl_3$) δ 1.13 (d, J=6.2 Hz, 3H), 1.25 (d, J=6.2 Hz, 3H), 2.31 (s, 6H), 3.66 (s, 3H), 4.97 (septet, J=6.2 Hz, 1H), 5.06 (s, 1H), 6.23 (s, 1H), 7.30–9.31 (m, 9H); $^{13}$C NMR ($CDCl_3$) δ 19.98, 20.02, 22.47, 22.72, 40.34, 51.67, 67.85, 103.69, 104.37, 120.22, 121.84, 125.25, 125.61, 128.97, 129.17, 130.11, 131.01, 131.08, 134.11, 145.29, 145.82, 148.17, 149.75, 150.35, 167.43, 168.46. Anal. Calcd for $C_{26}H_{27}N_3O_7$: C, 63.28; H, 5.47. Found: C, 63.18; H, 5.26.

Methyl 1-Methylethyl 1,4-Dihydro-2,6-dimethyl-4-{3-[(Z)-N-(3-trifluoromethylphenylmethylene)-N-oxo-$\lambda^5$-azanyl]phenyl}-3,5-pyridinedicarboxylate (85)

The reaction of hydroxylamine 82 (0.71 g, 2 mmol) with α,α,α-trifluoro-m-tolualdehyde (60) (0.348 g, 2 mmol) afforded, after workup, a light yellow solid. The crude product was recrystallized from ether/petroleum ether to obtain 0.80 g (1.55 mmol, 78%) of 85 as a white crystalline solid: mp 127°–129° C.; IR ($CH_2Cl_2$) 3440, 2980, 1698, 1624, 1558, 1475, 1332, 1300, 1215, 1100, 1018, 810 cm$^{-1}$; $^1$H NMR ($CDCl_3$) δ 1.14 (d, J=6.2 Hz, 3H), 1.26 (d, J=6.2 Hz, 3H), 2.29 (s, 6H), 3.65 (s, 3H), 4.97 (septet, J=6.2 Hz, 1H), 5.08 (s, 1H), 6.47 (br s, 1H), 7.28–8.76 (m, 9H); $^{13}$C NMR ($CDCl_3$) δ 19.48, 21.99, 22.22, 39.98, 51.15, 67.31, 102.99, 103.70, 119.43, 121.55, 125.52, 125.55, 127.22, 128.56, 129.28, 130.43, 131.46, 131.92, 133.40, 144.79, 145.33, 148.92, 149.91, 167.01, 168.03. Anal. Calcd for $C_{27}H_{27}N_2O_5F_3$: C, 62.79; H, 5.23. Found: C, 62.68; H, 5.02.

Methyl 1-Methylethyl 1,4-Dihydro-2,6-dimethyl-4-{3-[((Z)-N-(2-pyridylmethylene)-$\lambda^5$-azanyl]phenyl}-3,5-pyridinedicarboxylate (86)

The reaction of hydroxylamine 82 (1.76 g, 5 mmol) with 2-pyridine-carboxaldehyde (63) (0.54 g, 5 mmol) afforded, after workup, a yellow oil. The crude product was purified by flash chromatography with ethyl acetate as the eluant to obtain 1.61 g (3.58 mmol, 72%) of 86 as a yellow gum: IR ($CH_2Cl_2$) 3440, 2980, 1697, 1622, 1482, 1550, 1475, 1385, 1300, 1218, 1100, 1017 cm$^{-1}$; $^1$H NMR ($CDCl_3$) δ 1.08 (d, J=6.2 Hz, 3H), 1.20 (d, J=6.2 Hz, 3H), 2.25 (s, 6H), 3.59 (s, 3H), 4.92 (septet, J=6.2 Hz, 1H), 5.03 (s, 1H), 6.81 (br s, 1H), 7.26–9.28 (m, 9H); $^{13}$C NMR ($CDCl_3$) δ 19.80, 19.84, 22.44, 22.71, 40.46, 51.61, 67.76, 103.35, 104.06, 119.94, 121.81, 124.57, 125.21, 129.08, 131.04, 136.20, 137.54, 145.49, 146.02, 149.21, 150.28, 150.39, 167.52, 168.56. Anal. Calcd for $C_{25}H_{27}N_3O_5$: C, 66.81; H, 6.01. Found: C, 66.63; H, 6.05.

Methyl 1-Methylethyl 1,4-Dihydro-2,6-dimethyl-4-{3-[(Z)-N-oxo-N-(2-thienylmethylene)-$\lambda^5$-azanyl]phenyl}-3,5-pyridinedicarboxylate (87)

The reaction of hydroxylamine 82 (0.71 g, 2 mmol) with 2-thiophenecarboxaldehyde (64) (0.224 g, 2 mmol) afforded after workup, a light yellow oil. The crude product was purified by flash chromatography with 1:1 ethyl acetate/petroleum ether as the eluant to obtain 0.64 g (1.41 mmol, 71%) of 87 as a light yellow oil. The oil crystallized from ether/pentane to yield yellow crystalline solid: mp 106°–109° C.; IR ($CH_2Cl_2$) 3440, 2940, 1695, 1620, 1555, 1470, 1375, 1300, 1215, 1100 cm$^{-1}$; $^1$H NMR ($CDCl_3$) δ 1.10 (d, J=6.2 Hz, 3H), 1.22 (d, J=6.2 Hz, 3H), 2.27 (s, 6H), 3.61 (s, 3H), 4.94 (septet, J=6.2 Hz, 1H), 5.06 (s, 1H), 6.98 (s, 1H), 7.17–7.77 (m, 7H), 8.44 (s, 1H); $^{13}$C NMR ($CDCl_3$) δ 19.87, 22.49, 22.74, 40.59, 51.54, 67.68, 103.30, 104.00, 119.18, 121.52, 127.64, 128,95, 129.76, 130.60, 130.66, 131.78, 133.49, 145.64, 146.13, 147.07, 150.57, 167.62, 168.64. Anal. Calcd for $C_{24}H_{26}N_2O_5S$: C, 63.43; H, 5.72. Found: C, 63.26; H, 5.72.

N-(3-Hydroxymethylphenyl)hydroxylamine (91)

To a solution of 3-nitrobenzyl alcohol (90) (1.53 g, 10 mmol) and $NH_4Cl$ (1.3 g, 24.3 mmol) in 86% aqueous ethanol (88 mL) was added zinc powder (2.6 g, 39.8 mmol). The resulting mixture was stirred vigorously at room temperature for 50 min. The mixture was filtered, and the solvent was poured into dichloromethane (450 mL). The solution was washed with water (10 mL) and dried ($MgSO_4$), and the solvent was concentrated to about 15 mL with a rotary evaporator. The resulting solution was used in subsequent reactions without further purifications.

General Procedures for the Preparation of Nitrones 92-96

To a solution of N-(3-hydroxymethylphenyl)hydroxylamine (91) (10 mmol) in ethyl alcohol (15 mL) was added aldehyde (10 mmol) in anhydrous ethyl alcohol (25 mL) and Na$_2$SO$_4$ (0.60 g). The resulting mixture was stirred at room temperature until TLC analysis indicated no starting material (30 min-1 h). In the cases of product which precipitated from the reaction mixture, the product was collected and purified by recrystallization. In the other cases, the reaction mixture was diluted with dichloromethane (400 mL) and dried (MgSO$_4$), and the solvent was removed with a rotary evaporator to afford the crude product.

N-(3-Hydroxymethylphenyl)-α-(3-nitrophenyl)nitrone (92)

The reaction of hydroxylamine 91 (1.36 g, 10 mmol) with 3-nitrobenzaldehyde (57) (1.51 g, 10 mmol) afforded, after workup, a light yellow solid. The crude product was recrystallized from acetone/petroleum ether to obtain 1.90 g (6.98 mmol, 70%) of 92 as a pale yellow crystalline solid: mp 177°-179° C.; IR (Nujol) 3220, 1570, 1530, 1350, 1040, 800 cm$^{-1}$; $^1$H NMR (Me$_2$SO-d$_6$) δ 4.58 (d, J=5.6 Hz, 2H), 5.39 (t, J=4.8, 2H), 7.45-9.53 (m, 9H); $^{13}$C NMR (Me$_2$SO-d$_6$) δ 62.91, 119.87, 120.25, 122.98, 125.19, 128.68, 129.42, 130.47, 132.40, 132.94, 135.30, 144.73, 148.26, 148.73. Anal. Calcd for C$_{14}$H$_{12}$N$_2$O$_4$: C, 61.76; H, 4.41. Found: C, 61.99; H, 4.52.

N-(3-Hydroxymethylphenyl)-α-(4-nitrophenyl)nitrone (93)

The reaction of hydroxylamine 91 (1.36 g, 10 mmol) with 4-nitrobenzaldehyde (58) (1.51 g, 10 mmol) afforded, after workup, a red solid. The crude product was recrystallized from acetone/petroleum ether to obtain 2.21 g (8.1 mmol, 81%) of 93 as a red crystalline solid: mp 207°-209° C.; IR (Nujol) 3260, 1590, 1555, 1510, 1320, 1150, 1020, 860 cm$^{-1}$; $^1$H NMR (Me$_2$SO-d$_6$) δ 4.60 (d, J=5.6 Hz, 2H), 5.43 (t, J=5.7 Hz, 1H), 7.49-8.71 (m, 9H); $^{13}$C NMR (Me$_2$SO-d$_6$) δ 62.85, 119.99, 120.38, 124.29, 128.83, 129.47, 129.96, 132.70, 137.36, 144.79, 147.83, 148.94. Anal. Calcd for C$_{14}$H$_{12}$N$_2$O$_4$: C, 61.76; H, 4.41. Found: C, 62.09; H, 4.59.

N-(3-Hydroxymethylphenyl)-α-(2-nitrophenyl)nitrone (94)

The reaction of hydroxylamine 91 (1.36 g, 10 mmol) with 2-nitrobenzaldehyde (59) (1.51 g, 10 mmol) afforded, after workup, a yellow oil. The crude product was recrystallized from acetone/petroleum ether to obtain 1.74 g (6.4 mmol, 64%) of 94 as a yellow crystalline solid: mp 97°-99° C.; IR (CH$_2$Cl$_2$) 3605, 1570, 1525, 1340, 1155 cm$^{-1}$; $^1$H NMR (Me$_2$SO-d$_6$) δ 4.60 (d, J=5.6 Hz, 2H), 5.43 (t, J=5.6 Hz, 1H), 7.49-8.74 (m, 9H); $^{13}$C NMR (Me$_2$SO-d$_6$) δ 62.82, 119.85, 120.24, 124.84, 125.06, 128.85, 129.54, 129.79, 130.84, 131.28, 133.83, 144.86, 148.44, 148.55. Anal. Calcd for C$_{14}$H$_{12}$N$_2$O$_4$: C, 61.76; H, 4.41. Found: C, 61.85; H, 4.58.

N-(3-Hydroxymethylphenyl)-α-(2-pyridyl)nitrone (95)

The reaction of hydroxylamine 91 (1.36 g, 10 mmol) with 2-pyridinecarboxaldehyde (63) (1.07 g, 10 mmol) afforded, after workup, a yellow oil. The crude product was purified by passing through a short column of silica gel with 20:1 ethyl acetate/methanol as the eluant then recrystallized from acetone/petroleum ether to obtain 1.48 g (6.5 mmol, 65%) of 95 as a yellow crystalline solid: mp 117°-119° C.; IR (CH$_2$Cl$_2$) 3610, 3340, 1580, 1550, 1390, 1090 cm$^{-1}$; $^1$H NMR (CDCl$_3$) δ 4.53 (t, J=5.8, 1H), 4.65 (d, J=5.6 Hz, 2H), 7.28-9.27 (m, 9H); $^{13}$C NMR (CDCl$_3$) δ 63.86, 119.70, 120.37, 124.33, 124.91, 128.59, 129.31, 135.80, 137.25, 143.61, 148.62, 149.50, 149.84. Anal. Calcd for C$_{13}$H$_{12}$N$_2$O$_2$: C, 68.42; H, 5.26. Found: C, 68.52; H, 5.30.

N-(3-Hydroxymethylphenyl)-α-(5-nitro-2-furyl)nitrone (96)

The reaction of hydroxylamine 91 (1.36 g, 10 mmol) with 5-nitro-2-furaldehyde (65) (1.41 g, 10 mmol) afforded, after workup, a yellow solid. The crude product was recrystallized from acetone/petroleum ether to obtain 1.85 g (7.06 mmol, 71%) of 96 as a yellow crystalline solid: mp 187°-188° C.; IR (CH$_2$Cl$_2$) 3310, 1550, 1520, 1340, 1140, 1025, 1002, 802 cm$^{-1}$; $^1$H NMR (Me$_2$SO-d$_6$) δ 4.5 (d, J=5.6 Hz, 2H), 5.39 (t, J=5.6, 1H), 7.48-7.93 (m, 6H), 9.01 (s, 1H); $^{13}$C NMR (Me$_2$SO-d$_6$) δ 62.81, 115.39, 117.26, 119.49, 119.74, 123.41, 123.56, 129.22, 129.53, 144.88, 147.17, 150.15, 151.78. Anal. Calcd for C$_{12}$H$_{10}$N$_2$O$_5$: C, 54.96; H, 3.81. Found: C, 55.35; H, 3.88.

N-(3-Formylphenyl)-α-(3-nitrophenyl)nitrone (89)

To a solution of N-(3-hydroxymethylphenyl)-α-(3-nitrophenyl)nitrone (92) (1.38 g, 5.1 mmol) in dimethyl sulfoxide (50 mL) was added active manganese dioxide[82] (15 g). The resulting mixture was stirred at room temperature for 2½ h. The mixture was filtered and the solvent was slowly poured into water (200 mL), and the precipitate product was collected. The crude product was dissolved in dichloromethane, and the solution was washed with water (50 mL). The solution was then dried (MgSO$_4$), and the solvent was removed with a rotary evaporator. Recrystallization from dichloromethane/petroleum ether afforded 0.95 g (3.5 mmol, 69%) of 89 as a yellow crystalline solid: mp 195°-197° C.; IR (Nujol) 1690, 1525, 1340, 1150, 1060, 790 cm$^{-1}$; $^1$H NMR (Me$_2$SO-d$_6$) δ 7.77-8.74 (m, 7H), 8.93 (s, 1H), 9.53 (s, 1H), 10.10 (s, 1H); $^{13}$C NMR (Me$_2$SO-d$_6$) δ 122.44, 123.26, 125.58, 127.64, 130.67, 130.85, 131.76, 132.73, 133.15, 135.48, 137.54, 148.34, 149.15, 192.78; mass spectrum, m/e (relative intensity) 270 (M$^+$, 13.1), 254 (19.8), 119 (100), 91 (72.6), 77 (146.4); high resolution mass spectrum, m/e 270.0644 (calcd for C$_{14}$H$_{10}$N$_2$O$_4$, 270.0640).

Condensation of 89 with 2-Methoxyethyl Acetoacetate and 1-Methylethyl 3-Aminocrotonate To a solution of nitrone 89 (0.27 g, 1 mmol), 2-methoxyethyl acetoacetate (0.16 g, 1 mmol) and 1-methylethyl 3-aminocrotonate (0.144 g, 1 mmol) in anhydrous ethyl alcohol (35 mL) was added ammonium acetate (0.08 g, 1 mmol). The resulting mixture was heated at reflux for 32 h. The mixture was diluted with dichloromethane (100 mL) and dried (MgSO$_4$), and the solvent was removed with a rotary evaporator. The crude product was purified by flash chromatography with 1:1 ethyl acetate/petroleum ether to afford 0.14 g (0.26 mmol, 26%) of 68 as a light yellow crystalline solid. The mp, IR, $^1$H NMR, $^{13}$C NMR are all identical to those observed previously for compound 68.

In Vitro Tests

Both intracellular and extracellular Ca$^{2+}$ seem to be required for irreversible platelet aggregation. (Owen, N. E., et al., Am. J. Physiol. 239, H483 (1980); Owen, N. E., et al. Am. J. Physiol. 241, H613 (1981)). Thromboxane A2 (TXA2) is a platelet proaggregatory agent which may act in part by releasing Ca$^{2+}$ from intracellular stores in the platelet (Miller, O. V., et al. Prostaglandins, 13, 599 (1977); Gorman, R. R., Fed. Proc. 38, 83 (1979)) whereas prostacyclin (PGI$_2$), a platelet antiaggregatory agent, may act in part by increasing intracellular Ca$_2$+ sequestration in the platelet (Owen, N. E., et al., Am. J. Physiol., 239, H483 (1980)). Calcium channel blockers have been shown to prevent the influx of extracellular Ca$^{2+}$ in several cell types. They have recently been shown to inhibit ADP-, epinephrine- and collagen-induced platelet aggregation in vitro, although this inhibition may be due to the blocking of intracellular Ca$^{2+}$ mobilzation rather than influx of extracellular Ca$^{2+}$. Calcium channel blockers can also alter platelet function in vivo as administration of nifedipine, to humans has been shown to decrease ADP- and collagen-induced aggregation of platelets ex vivo and to increase the bleeding time.

Materials and Methods

Blood was drawn from the antecubital vein of healthy, fasted, aspirin-free (at least two weeks) human volunteers into one tenth volume of heparin (50 NIH units/ml). Platelet rich plasma was prepared by centrifugation for 10 minutes at 180×g and platelet poor plasma by further centrifugation for 10 minutes at 1086×g. The concentration of platelets was standardized to $3.0\pm0.2\times10^8$/ml.

Platelet aggregation was measured spectrophotometrically using a Sienco Model DP-247 dual channel aggregometer and recorded on a Sienco Model B-5000 dual channel recorder. A control was run in parallel with each novel compound synthesized. Meanwhile, a control was run in parallel with nimodipine which was used as an external standard. The 1000 microM or 250 microM solutions of the 4-(nitrone aryl)dihydropyridines and of the nimodipine in polyethylene glycol were prepared. The compounds in polyethylene glycol solution or polyethylene glycol alone were aliquoted into the aggregometry cuvettes. Immediately thereafter, 250 microliter of platelet rich plasma was added to cuvettes and the mixture incubated at 37° C., stirring at a constant speed of 800 RPM. After five minutes preincubation 25 microl of 10$^{-3}$ to 10$^{-5}$M ADP (in 0.9% saline) were added to both the experimental (compound containing) and control cuvette. Aggregations were terminated after 10–15 minutes by the addition of 25 microl of a 77 mM EDTA solution and cooling in an ice bath.

Results and Discussion

The novel compounds of the present invention were examined in vitro for inhibition of ADP-induced platelet aggregation of heparinized platelet rich plasma and nimodipine was used as an external standard (FIG. 1 and FIG. 2).

The results obtained employing 1000 microM concentrations of the compound are shown in FIG. 1. Compounds 70, 74, 76 were much more effective inhibitors of ADP-induced platelet aggregation than nimodipine. Compound 75 was less effective inhibitors of ADP-induced platelet aggregation compared to nimodipine.

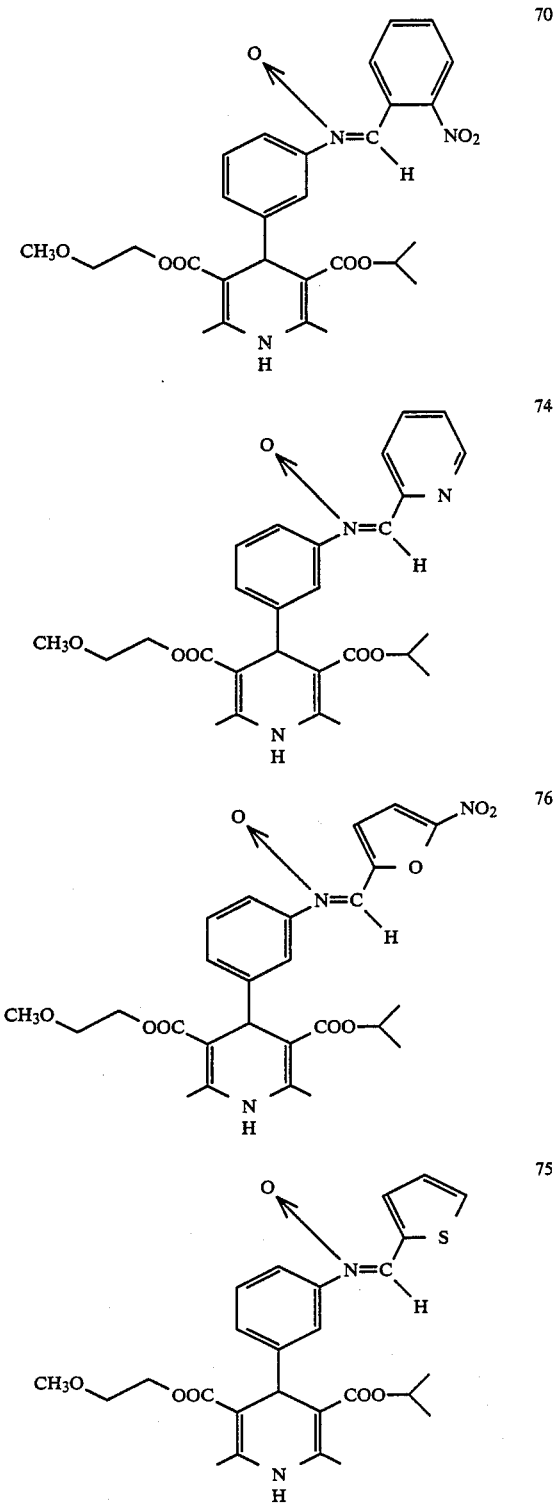

The results obtained employing 250 microM concentrations of the compound are shown in FIG. 2. Compound 70 was a more effective inhibitor of ADP-induced platelet aggregation than nimodipine.

It is clear that the electronegativity of the nitrone functionality is critical for the optimum biological activity.

In Vivo Metastasis

Compound 70 was tested in mice by tail vein injection of B16aNIH$_6$ tumor cells using the method described in methods in Cancer Research Chapter VII Academic Press, Inc. (1978). The procedure is described by Honn et al in Clinical and Expl. Metastasis 2, 61–72 (1984).

Compound 70 was dissolved in polyethylene glycol (PEG) at a concentration of 10 mg per ml. of the solution was injected or fed orally at various times. The mice (12 per group) were injected with compound 70 in an amount of 50 mg per kg as shown in Table III:

TABLE III

| | | | Treatment Before | Treatment After |
|---|---|---|---|---|
| 1 | Control PEG | ip | 6 hrs and 3 hrs | 45 min. |
| 2 | Compound 70 | oral | 4 hrs, 2 hrs, 30 min. | 45 min. |
| 3 | Compound 70 | ip | 6 hrs and 3 hrs | 45 min. |
| 4 | Compound 70 | ip | 24 hr, 6 hr, 1 hr. | 45 min. |

The results are shown in FIG. 3.

The data in FIG. 3 shows that Compound 70 at a 50 mg per kg dosage inhibits metastatic growth when given orally and interperitoneally (ip). The best results were achieved at 24, 6 and 1 hour ip injections; however, three of twelve mice did not survive to termination and thus some adjustment of dosage (number of injections) may be necessary.

Based upon the foregoing data the compounds of the present invention have in vitro utility and in vivo utility in animals. The most preferred compound is compound 70.

We claim:

1. A 4-(nitrone aryl)dihydropyridine compound of the formula:

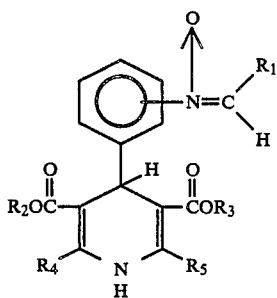

wherein R$_1$ is selected from substituted and unsubstituted aryl groups and carbon attached substituted and unsubstituted heterocyclic groups selected from the group consisting of thienyl, furyl, pyridyl and pyrrolyl, wherein the substituted aryl and substituted heterocyclic groups are substituted with groups selected from chloro, nitro, methyl and trifluoromethyl groups and wherein R$_2$ and R$_3$ are selected from lower alkyl and alkoxy (lower alkyl) and wherein R$_4$ and R$_5$ are lower alkyl.

2. A 4-(nitrone aryl)dihydropyridine compound of the formula:

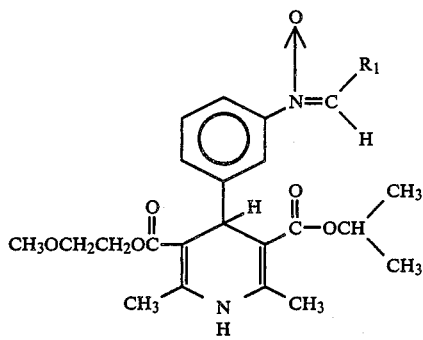

wherein R$_1$ is selected from substituted and unsubsituted aryl groups and carbon attached substituted and unsubstituted heterocyclic groups selected from the group consisting of thienyl, furyl, pyridyl and pyrrolyl, and wherein the substituted aryl and substituted heterocyclic groups are substituted with groups selected from chloro, nitro, methyl and trifluoromethyl groups.

3. The compound of claim 2 wherein R$_1$ is a substituted aryl group.

4. The compound of claim 3 wherein the substituted aryl group is a nitrophenyl group.

5. The compound of claim 4 wherein the nitrophenyl group is an o-nitrophenyl group.

6. The compound of claim 3 wherein the substituted aryl group is a n-trifluoromethylphenyl group.

7. The compound of claim 3 wherein the substituted phenyl group is a chlorophenyl group.

8. The compound of claim 7 wherein the chlorophenyl group is an o-chlorophenyl group.

9. The compound of claim 1 wherein the heterocyclic group is a substituted or unsubstituted pyridyl group.

10. The compound of claim 9 wherein the heterocyclic group is a pyridyl group.

11. The compound of claim 1 wherein the heterocyclic group is a substituted or unsubstituted thienyl group.

12. The compound of claim 1 wherein the heterocyclic group is a substituted or unsubstituted furyl group.

13. The compound of claim 1 wherein the heterocyclic group is a substituted or unsubstituted pyrrolyl group.

14. The compound of claim 13 wherein the pyrrolyl group is a N-methyl pyrrolyl group.

* * * * *